United States Patent [19]

Sato et al.

[11] Patent Number: 5,569,921
[45] Date of Patent: Oct. 29, 1996

[54] INFRARED OPTICAL PART AND MEASURING INSTRUMENT

[75] Inventors: Shuichi Sato; Hitoshi Sumiya; Katsuyuki Kawate; Jiro Katoh, all of Itami, Japan

[73] Assignee: Sumitomo Electric Industries, Ltd., Osaka, Japan

[21] Appl. No.: 244,635

[22] PCT Filed: Sep. 19, 1993

[86] PCT No.: PCT/JP93/01287

§ 371 Date: Jun. 6, 1994

§ 102(e) Date: Jun. 6, 1994

[87] PCT Pub. No.: WO94/08224

PCT Pub. Date: Apr. 14, 1994

[30] Foreign Application Priority Data

Oct. 7, 1992 [JP] Japan ................................. 4-296326

[51] Int. Cl.⁶ ............................ G01N 21/27; G02B 1/02
[52] U.S. Cl. ................. 250/339.01; 250/339.07; 250/339.11; 250/339.12; 250/341.2
[58] Field of Search .................. 250/339.01, 339.07, 250/339.11, 339.12, 341.2

[56] References Cited

U.S. PATENT DOCUMENTS 5,057,691 10/1991 Kaihara et al. ............... 250/339.11
5,245,189 9/1993 Satoh et al. .................... 250/343

FOREIGN PATENT DOCUMENTS

| 0503934 | 9/1992 | European Pat. Off. . |
| 0529999 | 3/1993 | European Pat. Off. . |
| 61-281946 | 12/1986 | Japan . |
| 62-2138 | 1/1987 | Japan . |
| 64-56401 | 3/1989 | Japan ............................... 250/339.07 |
| 4-116452 | 4/1992 | Japan . |
| 4-138340 | 5/1992 | Japan ............................... 250/339.07 |
| 4-178539 | 6/1992 | Japan . |
| 4-234001 | 8/1992 | Japan . |
| 92/14542 | 9/1992 | WIPO . |

*Primary Examiner*—Constantine Hannaher
*Attorney, Agent, or Firm*—Wenderoth, Lind & Ponack

[57] ABSTRACT

Using a synthetic diamond as the material of a prism allows ATR spectral analysis to be conducted only by pushing it into contact with a measuring object for measurement at places with poor environment, measurement of structures themselves, or measurement of samples sticking to cloths or the like, an optical part such as an infrared microscope system oriented sample plate can withstand a large number of times of use. A measuring instrument employs an attenuated total reflection (ATR) prism 14 of the synthetic diamond, having a nitrogen content of not more than 3 ppm and a boron content of not more than 3 ppm as contained in crystal. In combination with this prism 14 are optical-use mirrors 12, 17, lenses 13, 16, or optical fiber, whereby measurement can be conducted by pushing the prism into direct contact with a sample 15 without using a holder or the like.

3 Claims, 4 Drawing Sheets

INFRARED OPTICAL PART AND MEASURING INSTRUMENT

TECHNICAL FIELD

The present invention relates to optical parts primarily for use in infrared spectral analysis and, more particularly, to an ATR (attenuated total reflectance) prism capable of measuring ATR spectra only by bringing the prism into pressure contact with a measuring object. The present invention also relates to parts such as sample plates for holding a sample to be used in measuring absorption spectra of small-quantity impurities or small portions of organic substances with a microscope type infrared spectrometer.

PRIOR ART

In a conventional infrared ATR spectrometer, first, with the use of a prism 1 as shown in FIG. 1, a sample 2, processed into a thin piece, is put into contact with a prism surface 3, on which measuring light 4 is incident. Then, upon total reflection of the light by an interface 3 between the sample and the prism, there occurs a penetration which causes an absorption unique to the sample. By measuring the spectrum of transmitted light 5 that has undergone the absorption, the sample and impurities contained therein are measured. It is to be noted that details of this method are as described in "Development of Transparent Optical Parts for Large Output $CO_2$ Laser," by Takeo Miyata.

Conventionally, as the material of this prism 1 for infrared ATR spectral analysis, such substances as shown in Table 1 have been available. As the material of the prism 1, among other natural diamonds, the optimum one is called type IIa, which exhibits no absorption in the infrared region.

On the other hand, whereas diamonds have almost no defects in terms of material quality, the type suitable for infrared spectral analysis among diamonds is the one so called type IIa that shows no absorption in the infrared region. This type of diamond is as small in quantity as 1–2% of the total yield of natural diamonds, such that those of large size, as much as several millimeters, a size sufficient of diamond to be used as prisms, are very rare in yield and, almost unavailable in actual cases.

SUMMARY OF THE INVENTION

The present invention provides an infrared optical part and a measuring instrument employing the same which solves the above described problems and which allows ATR spectral analysis to be conducted only by pushing a prism into contact with a measuring object for measurement at any places with poor environment, measurement of structures themselves, or measurement of samples that have stuck to cloths or the like.

As a result of vigorous studies to solve the forgoing problems, the present inventors have found the following:

(1) Among synthetic diamonds used, one having a nitrogen content of not more than 3 ppm and a boron content of not more than 3 ppm contained as impurities, was found to be suitable for ATR prisms.

(2) A compact measuring instrument was fabricated by combining an optical-use mirror or optical fiber or optical-use lens and the aforementioned synthetic diamond, which makes it possible to conduct measurement by pushing the instrument into direct contact with the sample.

(3) To obtain better incidence or convergence of ATR measuring light, the prism was formed into a shape covered with small planes that will not reflect ATR light.

TABLE 1

| Material | Transmission region (μm) | Refractive index at 10.6 μm | Thermal conductivity W/cmk | Problems |
| --- | --- | --- | --- | --- |
| Ge | 1.8–23 | 4.02 | 0.59 | Transmission region narrow |
| CdTe | 0.9–30 | 2.69 | 0.06 | Toxic, low in thermal conductivity |
| GaAs | 0.9–18 | 3.30 | 0.48 | Transmission region narrow |
| ZnSe | 0.5–22 | 2.40 | 0.18 | Transmission region narrow, liable to be damaged |
| KBr | 0.2–30 | 1.54 | 0.048 | Deliquescent, liable to be damaged |
| KCl | 0.2–24 | 1.47 | 0.065 | Deliquescent, liable to be damaged |
| KRS-5 | 0.5–40 | 2.38 | 0.054 | Deliquescent, soft, toxic |
| Natural IIa diamond | 0.25– | 2.38 | 20.0 | Almost unavailable in large size |

However, as shown in Table 1, conventionally available substances except diamonds have had some problems such as: (1) narrow transmission region; (2) toxic; (3) liable to damage; and (4) deliquescent.

On account of the above defects, it has hitherto been quite difficult to conduct measurement in non-air-conditioned, poor-environment rooms, or at any places outdoors. Moreover, their insufficiency in durability or strength makes it difficult to push the prism into direct contact with the sample itself for measurement, which requires the sample to be formed into a thin piece and put into contact with the prism by using a special holder.

(4) To obtain better convergence or measuring accuracy of incident light or ATR measuring light, a lens, a prism, or a mirror formed of a substance with a diamond-equivalent refractive index (ZnSe, KRS-5, etc.) was combined with a diamond ATR prism in contact with each other.

It is noted that the diamond ATR prism of the present invention is usable also as a common prism, and that the spectral analysis system of the invention allows measurement even in visual and ultraviolet regions without being limited to the infrared region.

Further, the inventors have found that an infrared microscope system oriented sample plate fabricated by using the following synthetic diamonds are appropriate as a sample plate to be used in infrared spectral analysis for measuring absorption spectra of small-quantity impurities and small portions:

(5) A synthetic diamond having a nitrogen content of not more than 3 ppm and a boron content of not more than 3 ppm as contained in crystal was used to serve as an infrared microscope system oriented sample plate having a parallelism between incident surface and transmitting surface of measuring light of not more than one arc minute.

(6) The incident surface of the infrared microscope system oriented sample plate is preferably provided with a concave hole for holding a measuring sample, and the hole preferably has a depth of 0.01–100 μm and a surface-precision at the bottom of not more than 0.5 μm.

This hole is fabricated by using an energy line such as ion beams and electron beams.

Some advantageous functions and effects of the present invention are described in detail below.

(1) Function of using a synthetic diamond having a nitrogen content of not more than 3 ppm and a boron content of not more than 3 ppm:

Among diamonds, those suitable for infrared spectral analysis are the so-called type IIa, which exhibit no absorption in the infrared region. This type of diamond is as small in quantity as 1–2% of the yield of natural diamonds, such that those of a large size, as much as several millimeters sufficient to be used for prisms are very rare in yield, and virtually non-existent. Thus, the present invention has employed a synthetic diamond that can be synthesized into a large size.

Since this synthetic diamond generally uses a metal solvent of Fe, Ni, Co, or the like, nitrogen and boron atoms existing in the solvent are incorporated into crystals, so that absorption peaks appear in the infrared region.

Absorption by the nitrogen element appears as a sharp peak at $1332$ cm$^{-1}$ and a gentle, large peak of $1130$ cm$^{-1}$. The former, with the use of an FTIR (Fourier Transform Infrared Radiation) spectral analysis system, appears as a pseudo peak, resulting in a measurement error. The latter's large absorption peak, in the case of prisms, causes the ratio of (transmitted measuring light)/(incident light) to lower because of a long light path of infrared light, with an increased S/N ratio and an also increased measurement error. Prisms will be affected to a greater extent by the latter, in which case diamonds suitable for the material have been found to have a nitrogen content of not more than 3 ppm.

Further, absorption by the boron element shows sharp absorptions at $2935$ cm$^{-1}$, $2807$ cm$^{-1}$, $2459$ cm$^{-1}$, and $1332$ cm$^{-1}$, such that wrong measurement results may be derived as pseudo peaks. However, it has been found that such a problem will not occur when the boron content is not more than 3 ppm.

(2) Effect of fabricating a compact probe in combination of a synthetic diamond and an optical-use mirror and the like:

In measurement in which the prism is put into direct contact with a measuring object, the most superior material in durability and corrosion resistance is diamond, so that the present invention employs a synthetic diamond with the advantages as described in the preceding paragraph (1).

In the conventional ATR measuring method, as shown in FIG. 1, measurement was conducted in a state such that the sample 2 was processed into a thin piece or a flat plate and put into contact with the prism surface 3 and pushed thereagainst by a holder or the like.

In this case, samples which can be easily processed into a thin piece or flat plate are measurable. However, unmovable structures themselves or samples sticking to cloths or the like could not be measured as they were.

From this point of view, the present invention has found three ways to solve such problems:

(a) For measurement with an arrangement where a diamond prism is installed downward and a sample is set thereon and pushed thereagainst by a jig, etc., a mirror or a lens is fixedly installed to improve the introduction of incident light onto the diamond prism and convergence of the transmission side measuring light. A typical example of this is illustrated in FIG. 2.

Referring to FIG. 2, designated by numeral 14 is a prism, and by 15 is a sample. Incident light 11, which is incident vertically from the underside, enters into the prism 14 as converged by a converging mirror 12 and a converging lens 13, where it is reflected and absorbed at the interface on the prism 14 with the sample 15. The light 11 is transmitted through the prism 14 into measuring light 18, which is led downward by a converging lens 16 and a converging mirror 17, and thus subjected to measurement. In this way a small probe can be fabricated in a combination of a prism, mirrors, and lenses.

(b) For measurement with an arrangement where a diamond prism is installed upward, a sample is set downward thereof, and the diamond prism itself is lowered and pushed against the sample. A mirror or a lens is arranged so that measurement can be conducted even with a slide of the prism. A typical example of this is illustrated in FIG. 3. Referring to FIG. 3, designated by numeral 24 is a prism, 25 is a sample, and 26 is a sample base on which the sample is to be placed. Incident light 21, which is incident in the horizontal direction, is led downward by a turning mirror 22 and applied to the prism 24 by a converging mirror 23. If the prism 24 is lowered to be pushed against the sample 25, the incident light 21 is reflected and absorbed at the interface between the prism and the sample. Measuring light 29 is lead upward by a converging mirror 27 and led toward the horizontal direction by a turning mirror 28. With this arrangement, even if the prism 24 moves up and down, measurement can be conducted with the place to which the measuring light 29 is led unchanged.

(c) To make a diamond prism movable to any arbitrary place, an optical fiber is used for the introduction and transfer of incident light, and for convergence and transfer of transmitted measuring light. A typical example of this is illustrated in FIG. 4.

Referring to FIG. 4, incident light 31 is introduced to a prism 33 through an optical fiber 32, reflected and absorbed at the interface between the prism 33 and a sample 34, conducted out of the prism 33, passing through an optical fiber 35 as measuring light 36, and thus led to a measuring instrument (not shown). Since the probe and the measuring instrument are connected by an optical fiber, the probe can be easily moved to a measuring point, facilitating the measurement.

(3) Function of forming the prism into a shape that it is covered with small planes that will not totally reflect light, to obtain better convergence of ATR measuring light:

Diamond has a high refractive index, so that it involves repeated reflection within the prism, which disadvantageously leads to a deteriorated convergence efficiency of ATR light. In the present invention, to better the efficiencies of incidence and convergence of light, the prism is covered with small planes so as to prevent reflection loss at the surface where the ATR light is applied to or emitted from the prism. A typical example of this is illustrated in FIG. 5. Referring to FIG. 5, incident light 41 is converged by a lens 42, entering a prism 43. Then the incident light is reflected at the interface between a sample 45 and the prism 43, and radiated out of the prism.

To reduce any loss that occurs when the ATR light reflected at the surface radiates out of the prism, the prism 43 is covered with small planes 44. Radiated measuring light 47 is turned by a mirror 46, and thus sent to the measuring system.

(4) Function of contact-combining a diamond and an optical part formed of a substance with a substantially diamond-equivalent refractive index:

Diamonds are so poor in workability that a curved surface cannot be obtained. Also, their prices are so high that unfavorably the greater the anvil, the higher the price. For this reason, a substance with a substantially diamond-equivalent refractive index (e.g. ZnGe, KRS5, etc.) is previously worked and contact-combined with a diamond, thereby preventing any loss in incidence and convergence of light. Further, partly replacing the diamond with these substances will allow a larger prism to be obtained, improving the measuring accuracy. An example is shown in FIG. 6.

Incident light 51 comes into a substance 53 with a diamond-equivalent refractive index, which has been provided with a curved surface and other processing, via a converging mirror 52, entering a diamond prism 54 without being reflected. It is then totally reflected at the interface with a sample 55, and thus emitted out of the substance 53 with a diamond-equivalent refractive index. In this emission, the substance 53 with a diamond-equivalent refractive index, having been worked into a curved surface, will involve almost no reflection loss. Emitted measuring light 57 is converged by a mirror 56.

(5) Effect of fabricating an infrared microscope system oriented sample plate having parallelism between an incident surface and a transmitting surface of measuring light of not more than one arc minute, by using a synthetic diamond having a nitrogen content of not more than 3 ppm and a boron content of not more than 3 ppm:

The infrared microscope system oriented sample plate of the present invention employs a synthetic diamond, so that it can be a superior sample plate by virtue of its high strength and poor reactivity with various types of samples.

In other words, since samples are ones dissolved into an acidic or alkaline liquid or other liquid, any of the materials as shown in Table 1 except the diamond is problematic in chemical stability, often resulting in restrictions in various aspects of samples such as its fabricating method and observation method.

It was not until recent years that the fine-processing technique of diamond was improved enough to be applied to infrared microscope system oriented sample plates. In more detail, the sample plate in the present invention, which is normally plate shaped, has a particular importance in its parallelism between upper and lower surfaces. If the upper and lower surfaces are spaced 2 mm, a parallelism of not more than 1 μm is required as the difference of their thickness. For example, when a sample is put into a sample recess 62 of an infrared microscope system oriented sample plate 61 as shown in FIG. 7 and observed by an infrared microscope spectrometer, it is required to set the parallelism between an incident surface 63 and a transmitting surface 64 within one arc minute.

(6) Function of forming a concave hole for holding a measuring sample on the incident surface of the sample plate:

The infrared microscope spectrometer oriented sample plate 61 of the present invention as shown in FIG. 7 is 1–5 mm ϕ in diameter, normally approximately 2–3 mm ϕ in diameter, and is provided with a sample recess 62, a concave hole, at its incident surface 63. The sample recess 62 is appropriately 0.5 mm ϕ in diameter and approximately 0.5–100μ in depth. Further, the surface precision at the bottom of the hole is preferably not more than 0.5 μm.

In conducting infrared spectral analysis, a measuring sample is charged into the sample recess 62, and a diamond disc without a concave portion is overlaid thereon and fixed as it is. In this state, infrared light is applied from the incident surface 63 side, where absorption in the infrared region of transmitted light that has permeated the sample recess is measured.

In addition, it is difficult to apply any mechanical method such as grinding to formation of such a hole as described above in the sample plate made from a synthetic diamond of the present invention. The hole is formed by an energy beam such as ion beams and electron beams.

BRIEF DESCRIPTION OF THE DRAWINGS

FIG. 7(B) is a longitudinal sectional view thereof.

THE BEST EMBODIMENTS FOR CARRYING OUT THE INVENTION (Example 1)

A high-purity single crystal was synthesized by using a temperature difference method under a pressure-temperature range such that diamond holds stable. An Fe-40 Co alloy was used for the solvent applied to the synthesis.

Figure 1:
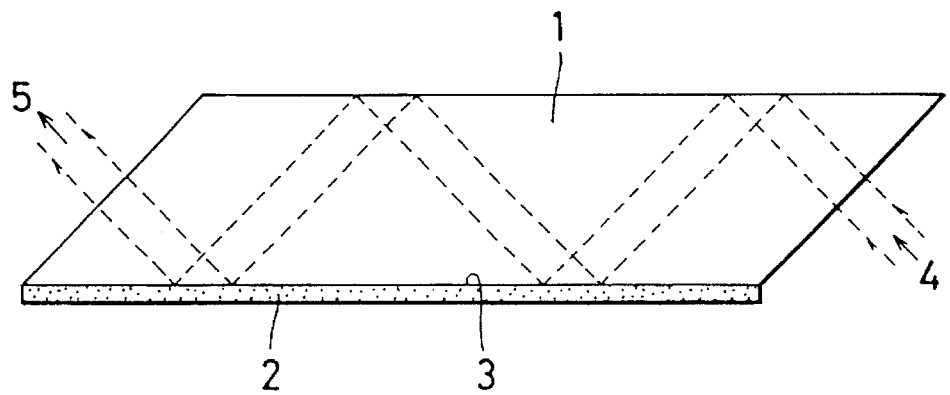
FIG. 1 is a front view showing a measuring method using a conventional ATR prism.
Figure 2:
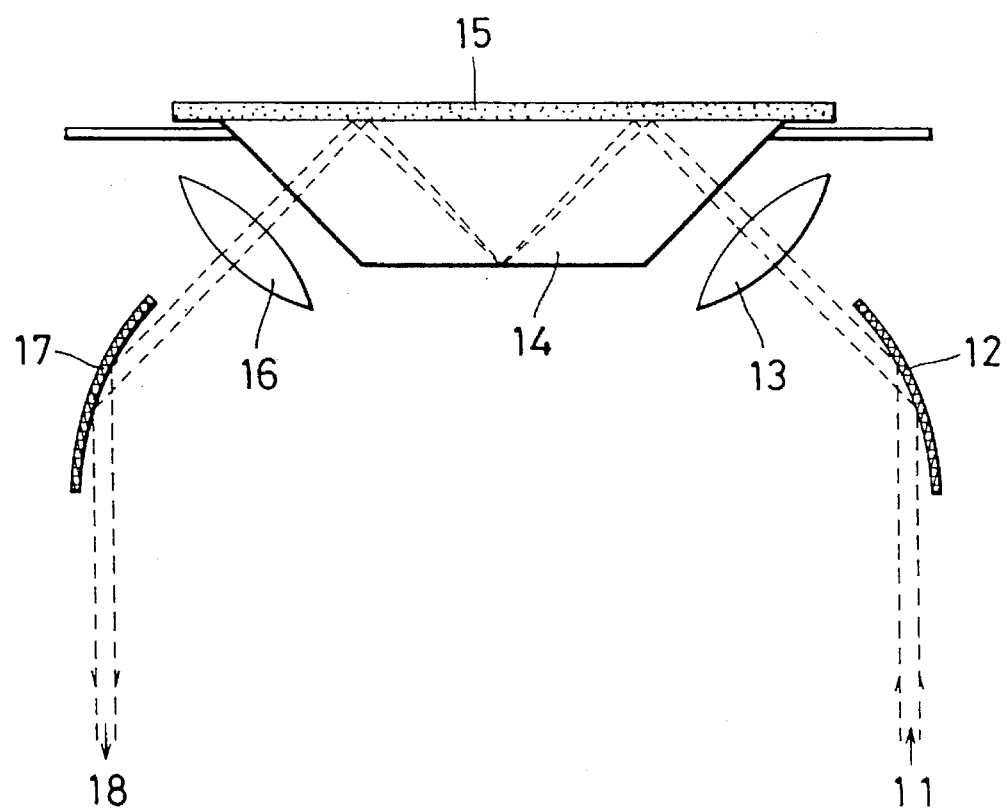
FIG. 2 is a front view showing an ATR measuring instrument according to the present invention in which a prism is fixed downward during measurement.

To remove nitrogen, an AlTi alloy was added. Also, to examine the effect of the boron element, a solvent metal incorporating materials of different purities was prepared and used for synthesis. The synthesized crystal was processed as shown in FIG. 2, and subjected to ATR spectrometer.

TABLE 2

| Item | | 1 | 2 | 3 | 4 | 5 |
|---|---|---|---|---|---|---|
| Nitrogen content (in crystal) | | 0.2 ppm | 3 ppm | 5 ppm | 3 ppm | 5 ppm |
| Boron content (in crystal) | | 0.2 ppm | 3 ppm | 3 ppm | 5 ppm | 5 ppm |
| Absorption peak | 1322 cm$^{-1}$ (due to nitrogen) | No | ← | Yes | No | Yes |
| | 1130 cm$^{-1}$ (due to nitrogen) | No | ← | Yes | No | Yes |
| | 2935 cm$^{-1}$ (due to boron) | No | ← | ← | Yes | ← |
| | 2807 cm$^{-1}$ (due to boron) | No | ← | ← | Yes | ← |
| | 2459 cm$^{-1}$ (due to boron) | No | ← | ← | Yes | ← |
| | | Example | Example | Comparative Example | Comparative Example | Comparative Example |

As seen from Table 2, it can be understood that the material having a nitrogen content of not more than 3 ppm and a boron content of not more than 3 ppm as contained in crystal is suitable for the ATR prism of the present invention.

(Example 2)

Figure 3:
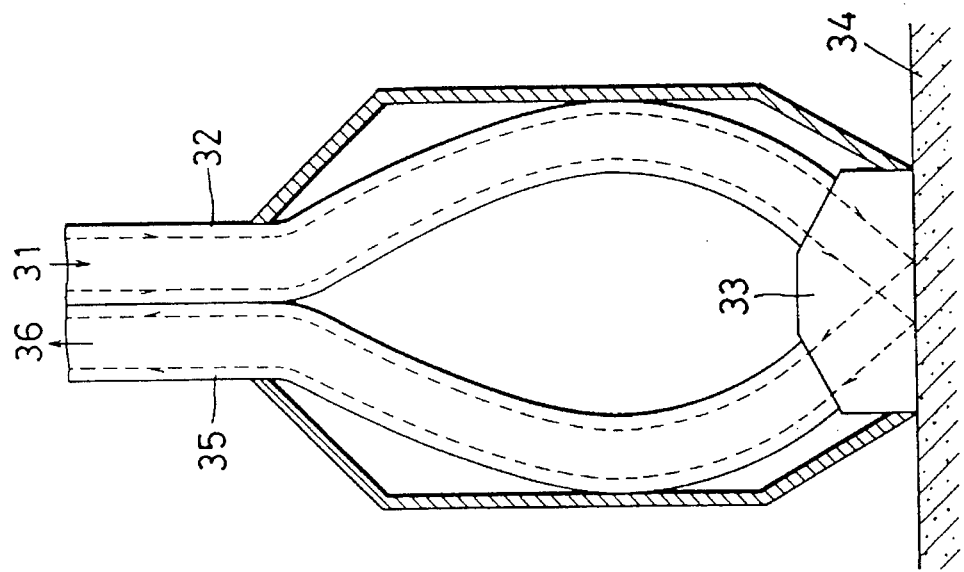
FIG. 3 is a front view showing an ATR measuring instrument according to the present invention in which a prism is located upward of a sample and lowered into contact therewith during measurement.
Figure 4:
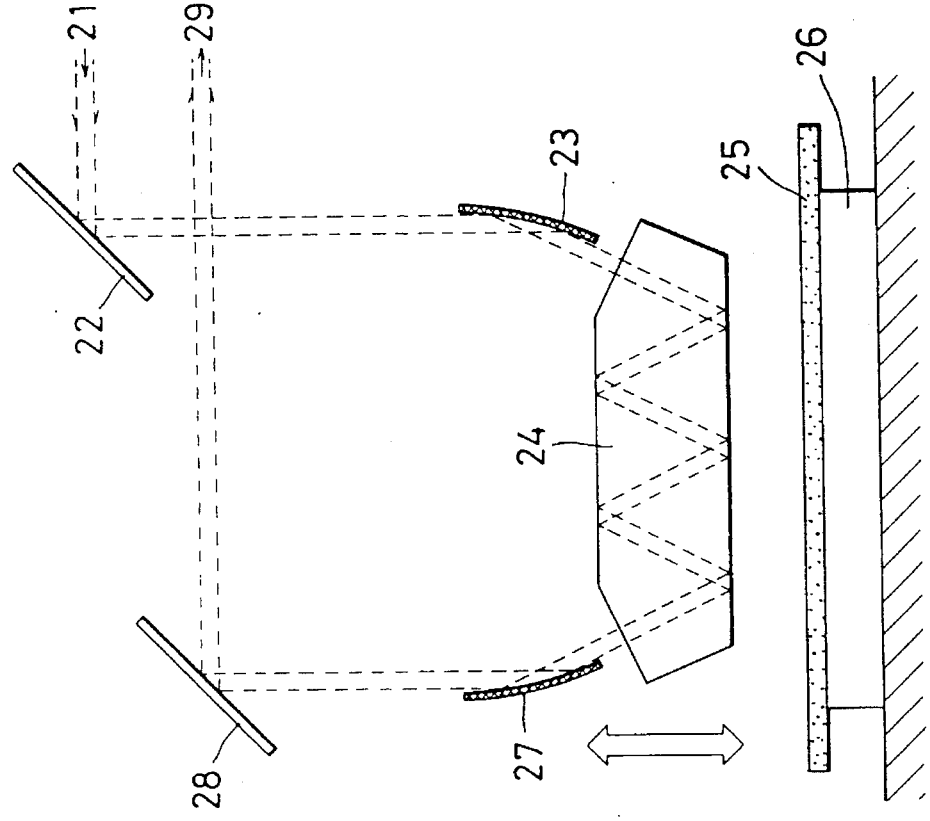
FIG. 4 is a front view showing an ATR measuring instrument according to the present invention in which a probe and a measuring instrument are connected to each other by an optical fiber.

The prism used in Experiment No. 1 in Example 1 was reworked into a shape as designated by numeral 24 in FIG. 3. The prism 24 was set as shown in FIG. 3, where incident light 21 was turned by a turning mirror 22, and enters into the prism 24 by a turning mirror 23. The set prism 24 was lowered and pushed against a sample 25 on a sample base 26.

The incident light 21 was repeatedly totally reflected at the interface between the prism 24 and the sample 25, thereby absorbed, and radiated in the direction opposite to that in incidence. Measuring light 29 that had permeated the prism 24 was converged by a Cassegrain mirror 27, and thus led to the measuring system by a turning mirror 28.

By the above method, ethylene glycol sticking to a PVC plate was successfully fixed.

(Example 3)

Figure 6:
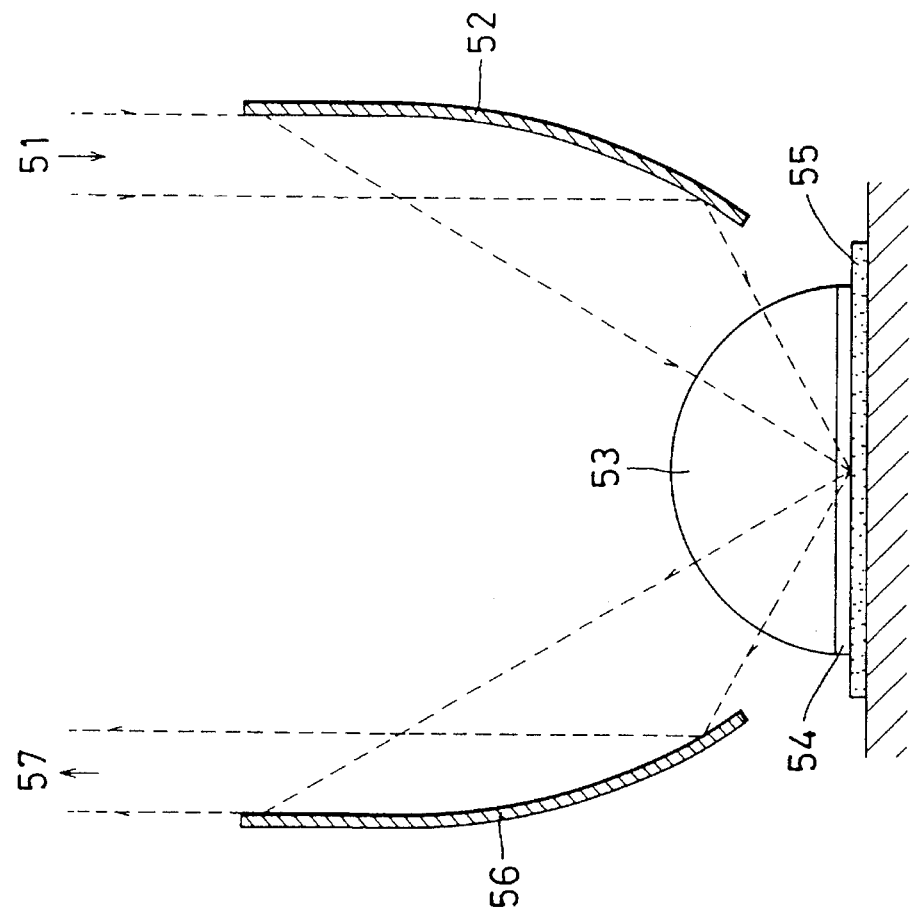
FIG. 6 is a front view showing a measuring instrument employing a prism in combination with a substance having a diamond-equivalent refractive index according to the present invention.
Figure 5:
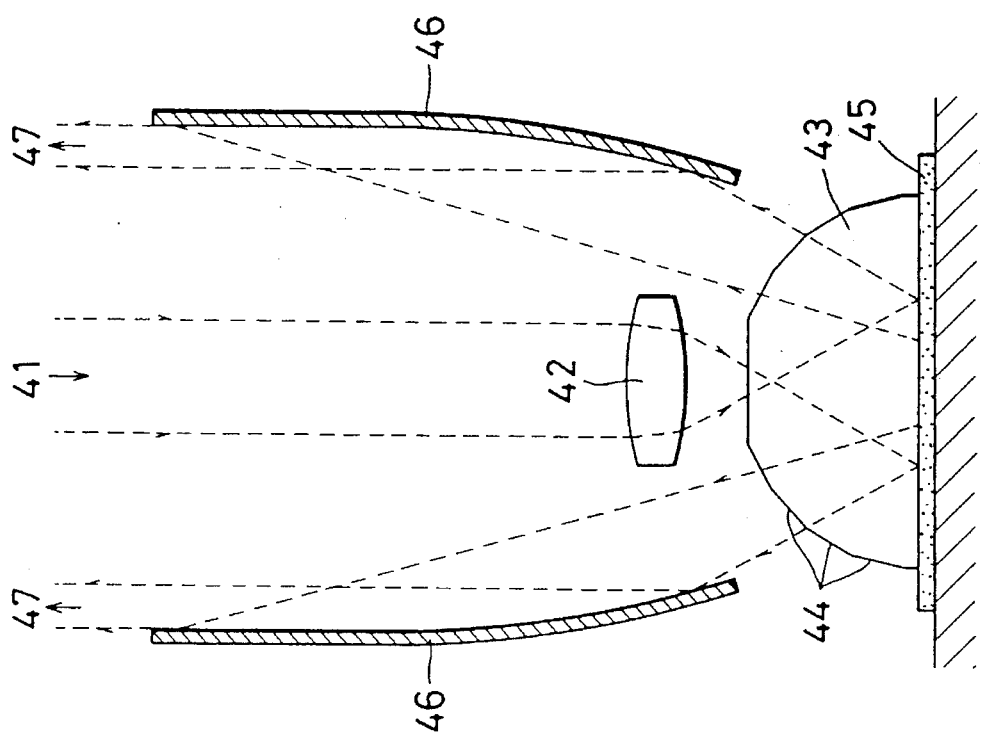
FIG. 5 is a front view showing a measuring instrument employing a prism covered with small planes according to the present invention.

As shown in FIG. 6, a semi-spherical KRS-5 lens 53 was put on and into close contact with a diamond disc 54. These were fixed and urged on a sample 55, in which state ATR measurement was conducted. Incident light 51 was applied vertically from the right side, converged by a mirror 52, and thus introduced into the semi-spherical lens 53 (KRS-5). The introduced light was not reflected at the interface with the diamond disc 54, but was reflected at the interface between the sample 55 and the diamond disc 54, and thereby absorbed. Reflected light was emitted outside without involving any reflection loss at the surface of the semi-spherical lens 53. Emitted measuring light 57 was led to the measuring system by a mirror 56.

By the above method, impurities mixed in a polyethylene film were determined successfully. Also, when measurement was conducted with the semi-spherical lens 53 removed, the strength of the measuring light 57 was so low that the impurities could not be determined.

(Example 4)

Figure 7A:
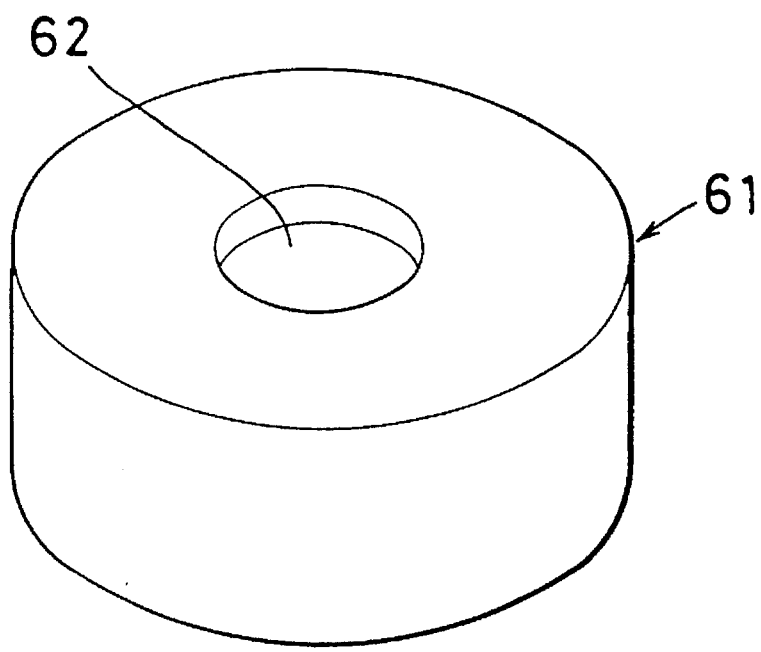
FIG. 7(A) and 7(B) show an infrared microscope system oriented material plate according to the present invention, where in FIG. 7(A) is a perspective view
Figure 7B:
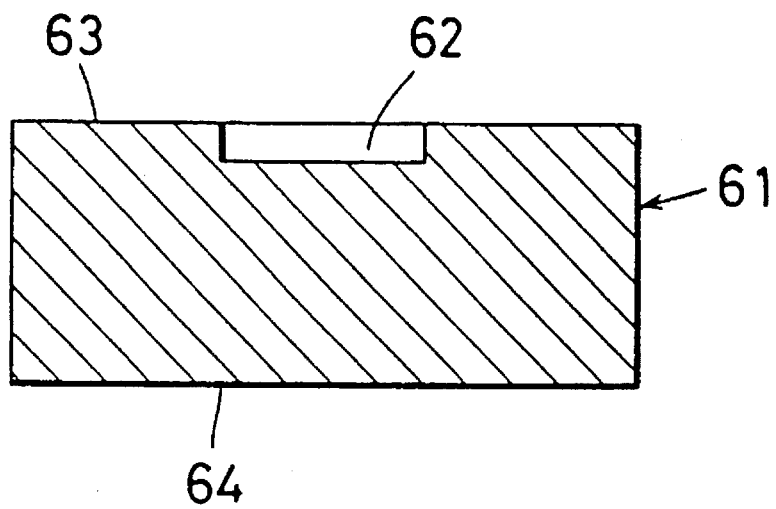

A diamond single crystal obtained in Example 1 was processed into a 2 mmφ-dia., 1 mm thick disc. The parallelism between an upper flat surface 63 and a lower surface 64 was arranged to be within 1 arc second. Further, a 0.5 mmφ-dia., 7 μm deep spot-faced hole was prepared in the center, thus fabricating a microscope type infrared spectral analysis oriented sample plate 61 as shown in FIG. 7. The surface roughness of the bottom surface of the hole, which serves as the sample recess 62, was Rmax 0.3 μm. A sample plate having no spot-faced hole in the center, which was of the same disc shape as the foregoing one, was also prepared.

An aqueous solution in which organic substances had been dissolved was filled into the spot-faced hole 62, and the sample plate having no spot-faced hole was overlaid thereon to prevent the sample from swelling due to surface tension. The assembly was installed in the measuring light path, where measurement was conducted. As a result, it has become possible to conduct accurate measurement without the sample plate itself melting into the aqueous solution, which was the case with conventional materials (e.g. KBr).

Further, even with samples that have been dissolved into an acid or alkali, which could not be measured because of their action of corroding the sample plate, use of the sample plate according to the present invention has made it possible to conduct infrared spectral analysis with such samples by the same method as described above.

Also, with samples having a small level of surface tension, measurement could be made only by inserting a sample into the spot-faced hole.

POSSIBILITY OF USE IN THE FIELD OF THE INVENTION

As described hereinabove, in the infrared spectral analysis using the ATR prism of the present invention, it has become possible to provide a prism superior in durability. Further, it has also become possible to conduct measurement by direct contact with a sample without the need of processing the sample into a thin piece and bringing it into contact with the prism by a holder or the like.

Further, the infrared microscope system oriented sample plate of the present invention is best-suited for a sample plate by virtue of its poor reactivity with various types of samples, and has a substantially improved durability in respect of the number of times of use by virtue of its high strength, as compared with conventional sample plates.

What is claimed is:

1. A measuring instrument, comprising:

an infrared optical part comprising an attenuated total reflectance prism comprising a synthetic diamond having a nitrogen content of not more than 3 ppm and a boron content of not more than 3 ppm contained in crystal;

said prism comprising an incident surface and a transmitting surface, at least one of said incident surface and said transmitting surface comprising a plurality of surfaces having no attenuated total reflection property; and at least one selected from the group consisting of an optical-use mirror, a lens and an optical fiber for providing incident light to and receiving transmitted light from said prism, whereby attenuated total reflection spectral analysis can be performed by moving said prism into contact with a sample.

2. The measuring instrument of claim 1, wherein said at least one selected from the group consisting of an optical-use mirror, a lens and an optical fiber comprises a converging lens for converging incident light onto said incident surface and at least one mirror for reflecting transmitted light transmitted from said transmitting surface, said transmitting surface comprising said plurality of surfaces having no attenuated reflection property.

3. The measuring instrument of claim 2, wherein said incident surface has said transmitting surface located on either side thereof, and said at least one mirror comprises a pair of optical-use mirrors.

\* \* \* \* \*